United States Patent
Hanashi et al.

(10) Patent No.: US 9,103,718 B2
(45) Date of Patent: *Aug. 11, 2015

(54) OPTICAL ANALYSIS DEVICE AND OPTICAL ANALYSIS METHOD USING A WAVELENGTH CHARACTERISTIC OF LIGHT OF A SINGLE LIGHT-EMITTING PARTICLE

(71) Applicant: OLYMPUS CORPORATION, Tokyo (JP)

(72) Inventors: Takuya Hanashi, Hachioji (JP); Tetsuya Tanabe, Tokyo (JP); Mitsushiro Yamaguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 157 days.

This patent is subject to a terminal disclaimer.

(21) Appl. No.: 13/888,868

(22) Filed: May 7, 2013

(65) Prior Publication Data

US 2013/0242307 A1 Sep. 19, 2013

Related U.S. Application Data

(63) Continuation of application No. PCT/JP2011/076151, filed on Nov. 14, 2011.

(30) Foreign Application Priority Data

Nov. 25, 2010 (JP) ................................. 2010-262267

(51) Int. Cl.
*G01N 21/00* (2006.01)
*G01N 21/17* (2006.01)
(Continued)

(52) U.S. Cl.
CPC ............... *G01J 1/16* (2013.01); *G01N 15/1463* (2013.01); *G01N 21/6452* (2013.01);
(Continued)

(58) Field of Classification Search
CPC ....... G01N 21/53; G01N 21/49; G01N 15/06; G01N 15/1012; G01N 15/1404; G01N 15/02; G01N 16/14; G01N 2015/03

USPC .................................................. 356/335–344
See application file for complete search history.

(56) References Cited

U.S. PATENT DOCUMENTS

| 4,251,733 A | 2/1981 | Hirleman, Jr. |
| 5,866,336 A | 2/1999 | Nazarenko et al. |

(Continued)

FOREIGN PATENT DOCUMENTS

| EP | 1 906 172 A1 | 4/2008 |
| JP | 4-337446 A | 11/1992 |

(Continued)

OTHER PUBLICATIONS

International Search Report dated Dec. 13, 2011, issued in related PCT/JP2011/069738.
(Continued)

*Primary Examiner* — Michael A Lyons
*Assistant Examiner* — Jarreas C Underwood
(74) *Attorney, Agent, or Firm* — Westerman, Hattori, Daniels & Adrian, LLP

(57) ABSTRACT

The inventive technique of detecting and analyzing light from a light-emitting particle in accordance with the scanning molecule counting method using an optical measurement with a confocal microscope or a multiphoton microscope is characterized by detecting intensities of components of two or more wavelength bands of light from a light detection region of an optical system with moving the position of the light detection region in a sample solution by changing the optical path of the optical system of the microscope; detecting individually signals of the light from each light-emitting particle in the intensities of the components of the two or more wavelength bands of the detected light; and identifying a kind of light-emitting particle based on the intensities of the components of the two or more wavelength bands of the signals of the light of the detected light-emitting particle.

12 Claims, 7 Drawing Sheets

Figures 1A, 1B, 1C:
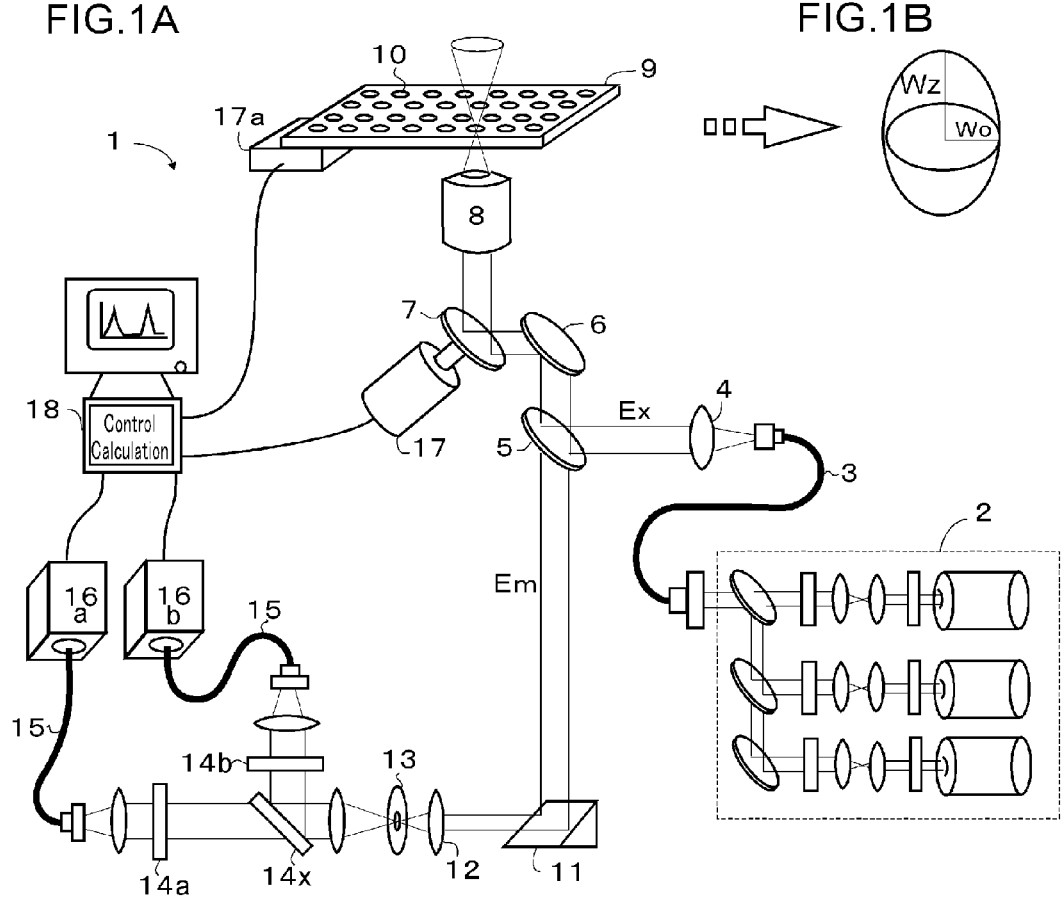

(51) Int. Cl.
*G01J 1/16* (2006.01)
*G01N 21/64* (2006.01)
*G01N 15/14* (2006.01)
*G02B 21/00* (2006.01)
*G01J 1/58* (2006.01)
*G01C 21/02* (2006.01)
*G02B 21/26* (2006.01)

(52) U.S. Cl.
CPC ....... *G01N 21/6458* (2013.01); *G02B 21/0076* (2013.01); *G01C 21/02* (2013.01); *G01J 1/58* (2013.01); *G01N 2021/6421* (2013.01); *G02B 21/0032* (2013.01); *G02B 21/26* (2013.01)

(56) References Cited

U.S. PATENT DOCUMENTS

| | | | |
|---|---|---|---|
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1* | 5/2002 | Harris et al. ............... 359/196.1 |
| 6,400,487 | B1 | 6/2002 | Harris et al. |
| 6,403,338 | B1 | 6/2002 | Knapp et al. |
| 6,586,193 | B2* | 7/2003 | Yguerabide et al. ............. 506/3 |
| 6,710,871 | B1 | 3/2004 | Goix |
| 6,856,391 | B2 | 2/2005 | Garab et al. |
| 6,927,401 | B1 | 8/2005 | Palo |
| 7,551,763 | B2* | 6/2009 | Calvin et al. ................. 382/133 |
| 8,284,484 | B2 | 10/2012 | Hoult et al. |
| 8,711,353 | B2* | 4/2014 | Kaye et al. .................... 356/342 |
| 8,804,119 | B2* | 8/2014 | Knox et al. ................... 356/337 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1* | 11/2003 | Sampas ......................... 356/318 |
| 2004/0022684 | A1 | 2/2004 | Heinze et al. |
| 2004/0051051 | A1* | 3/2004 | Kato et al. ................. 250/458.1 |
| 2004/0150880 | A1 | 8/2004 | Nakata et al. |
| 2004/0219535 | A1 | 11/2004 | Bell et al. |
| 2005/0179892 | A1 | 8/2005 | Gerstner et al. |
| 2005/0213090 | A1* | 9/2005 | Namba et al. ................. 356/318 |
| 2005/0260660 | A1 | 11/2005 | Van Dongen et al. |
| 2006/0078998 | A1 | 4/2006 | Puskas et al. |
| 2006/0158721 | A1* | 7/2006 | Nakata et al. ................. 359/386 |
| 2006/0256338 | A1 | 11/2006 | Gratton et al. |
| 2008/0052009 | A1 | 2/2008 | Chiu et al. |
| 2008/0117421 | A1 | 5/2008 | Yamaguchi et al. |
| 2008/0268548 | A1* | 10/2008 | Zuckerman ................... 436/172 |
| 2009/0159812 | A1* | 6/2009 | Livingston .................... 250/428 |
| 2009/0230324 | A1 | 9/2009 | Gratton et al. |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2011/0204258 | A1 | 8/2011 | Heller et al. |

FOREIGN PATENT DOCUMENTS

| | | | |
|---|---|---|---|
| JP | 2002-022640 | A | 1/2002 |
| JP | 2002-507762 | A | 3/2002 |
| JP | 2002-525579 | A | 8/2002 |
| JP | 2002-543414 | A | 12/2002 |
| JP | 2003-522969 | A | 7/2003 |
| JP | 2004-506192 | A | 2/2004 |
| JP | 3517241 | B2 | 4/2004 |
| JP | 2004-251814 | A | 9/2004 |
| JP | 2005-098876 | A | 4/2005 |
| JP | 2005-99662 | A | 4/2005 |
| JP | 2005-509857 | A | 4/2005 |
| JP | 2005-524051 | A | 8/2005 |
| JP | 2006-525517 | A | 11/2006 |
| JP | 2007-020565 | A | 2/2007 |
| JP | 4023523 | B2 | 12/2007 |
| JP | 2008-116440 | A | 5/2008 |
| JP | 2008-536093 | A | 9/2008 |
| JP | 2008-538609 | A | 10/2008 |
| JP | 2008-292371 | A | 12/2008 |
| JP | 2009-145242 | A | 7/2009 |
| JP | 2009-281831 | A | 12/2009 |
| JP | 2009-288161 | A | 12/2009 |
| JP | 2010-190730 | A | 9/2010 |
| JP | 2011-002415 | A | 1/2011 |
| WO | 98/16814 | A1 | 4/1998 |
| WO | 99/47963 | A1 | 9/1999 |
| WO | 00/66985 | A1 | 11/2000 |
| WO | 02/12864 | A1 | 2/2002 |
| WO | 2006/084283 | A2 | 8/2006 |
| WO | 2007/010803 | A1 | 1/2007 |
| WO | 2007/118209 | A2 | 10/2007 |
| WO | 2007/147159 | A2 | 12/2007 |
| WO | 2008/007580 | A1 | 1/2008 |
| WO | 2008/080417 | A1 | 7/2008 |
| WO | 2009/117033 | A2 | 9/2009 |
| WO | 2010/084719 | A1 | 7/2010 |
| WO | 2011/108369 | A1 | 9/2011 |
| WO | 2011/108371 | A1 | 9/2011 |

OTHER PUBLICATIONS

International Search Report dated Mar. 29, 2011, issued in related PCT/JP2011/053481.
Park, Mira et al., "Counting the Number of Fluorophores Labeled in Biomolecules by Observing the Fluoroscence-Intensity Transient of a Single Molecule" Bulletin of the Chemical Society of Japan, dated Aug. 30, 2005, vol. 78, No. 9, (p. 1612-1618).
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, (p. 1703-1713).
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry," Nucleic Acids Research, 1993, vol. 21, No. 4 (p. 803-806).
Keller, Richard et al., "Single-Molecule Fluorescence Analysis in Solution," Applied Spectroscopy, 1996, vol. 50, No. 7, (p. 12A-32A).
Lee, Yuan-Hsiang et al., "Laser-Induced Fluorescence Detection of a Single Molecule in a Capillary," Analytical Chemistry, dated Dec. 1, 1994, vol. 66, No. 23, (p. 4142-4149).
Li, Haitao et al., "Ultrasensitive Coincidence Fluorescence Detection of Single DNA Molecules," Analytical Chemistry, dated Apr. 1, 2003, vol. 75, No. 7, (p. 1664-1670).
Nie, Shuming et al., "Probing Individual Molecules with Confocal Fluorescence Microscopy," Science, dated Nov. 11, 1994, vol. 266, (p. 1018-1021).
Tahari, Abdel. "Fluorescence Correlation Spectroscopy: Ultrasensitive Detection in Clear and Turbid Media," University of Illinois, 2006, (p. 1-88).

(56) References Cited

OTHER PUBLICATIONS

Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, (p. 2157-2159).
U.S. Office Action dated Oct. 4, 2013, issued in related U.S. Appl. No. 13/596,243.
Schwille, Petra, et al., "Dual-Color Fluorescence Cross-Correlation Spectroscopy for Multicomponent Diffusional Analysis in Solution", Biophysical Journal, 1997, vol. 72, (p. 1878-1886).
International Search Report dated Nov. 29, 2011, issued in related PCT/JP2011/069440.
U.S. Office Action dated Nov. 29, 2013, issued in co-pending U.S. Appl. No. 13/788,972.
European Search Report dated Oct. 24, 2013, issued in related EP application No. 11823457.4.
Japanese Office Action dated Dec. 18, 2012 issued in related JP application No. 2012-503060; w/ English Translation (6 pages).
International Search Report Nov. 29, 2011, issued in related PCT/JP2011/072939.
Masataka Kinjo, "Single molecule protein, nucleic acid, and enzyme assays and their procedures Single molecule detection by fluorescence correlation spectroscopy", Protein, Nucleic acid Enzyme vol. 44, No. 9, 1999, pp. 1431-1438.
F. J. Meyer-Alms, "10 Nanoparticle Immunoassays: A new Method for Use in Molecular Diagnostics and High Troughput Pharmaceutical Screening based on Fluorescence Correlation Spectroscopy", edited by R. Rigler, Springer, Berlin, pp. 204-224, (2000).
Peet Kask et al., "Fluorescence-intensity distribution analysis and its application in biomolecular detection technology", PNAS, vol. 96, No. 24, Nov. 23, 1999, pp. 13756-13761.
International Search Report of PCT/JP2011/076151, mailing date of Feb. 14, 2012.
Notice of Allowance dated Sep. 10, 2014, issued in related U.S. Appl. No. 13/789,111 (45 pages).
European Office Notice dated Nov. 24, 2014, issued in corresponding EP Application No. 11843762.3 (7 pages).
Chinese Office Action dated Jun. 27, 2014, issued in related Chinese Patent Application No. 201180043161.3, with English Translation (14 pages).
Office Action dated Jul. 30, 2014, issued in corresponding Chinese Patent Application No. 201180057025.X, with English Translation (17pages).
Office Action dated Sep. 26, 2014, issued in related Chinese Patent Application No. 201180043734.2, with English Translation (10 pages).
Communication pursuant to Article 94(3) EPC dated Jul. 28, 2014, issued in corresponding European Patent Application No. 11823457.4 (4 pages).
European Official Communication dated Jul. 14, 2014, issued in related European Patent Application No. 11843762.3 (10 pages).
Itoh et al., "A New Method for Detection of Influenza Viruses by Single Particle-Recognition Based on the Principle of Fluorescence Correlation Spectroscopy," Chemistry and Biology, 2009, vol. 47, No. 12, (p. 823-830); with English Summary.
Noriko Kato et al., "A single molecule analyzer that enable new analysis of DNA and protein interactions", Gene Medicine, vol. 6, No. 2, 2002, pp. 271-277; with English Summary.
Geng, X. et al., "Morphology and expression of skeleton protein in cortex neuron of mice cultured in vitro at different temperatures", Chinese Journal of Clinical Rehabilitation, vol. 10, No. 29, Aug. 10, 2006, Cited in Chinese Office Action dated Jan. 6, 2015, with English abstract.
Office Action dated Jan. 6, 2015, issued in corresponding Chinese Patent Application No. 201180043161.3, with English translation (14 pages).
Extended European Search Report dated Oct. 20, 2014, issued in related EP Application No. 12770835.2 (10 pages).
Office Action dated Mar. 23, 2015, issued in Japanese Patent Application No. 201180057025.X, with English translation (18 pages).
Notice of Reasons for Rejection dated Jun. 9, 2015, issued in Japanese Patent Application No. 2012-532942 with English translation (8 pages).

\* cited by examiner

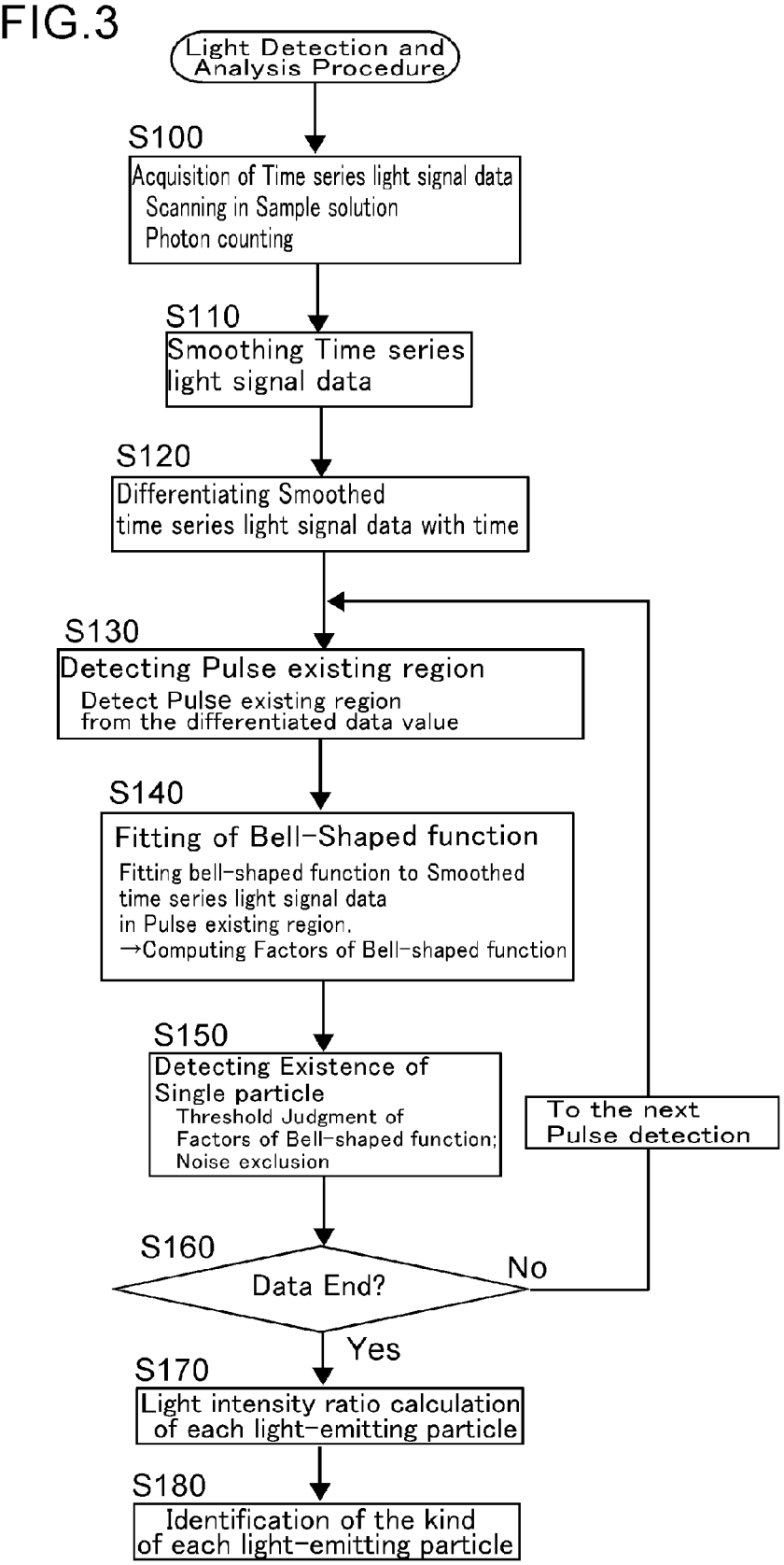

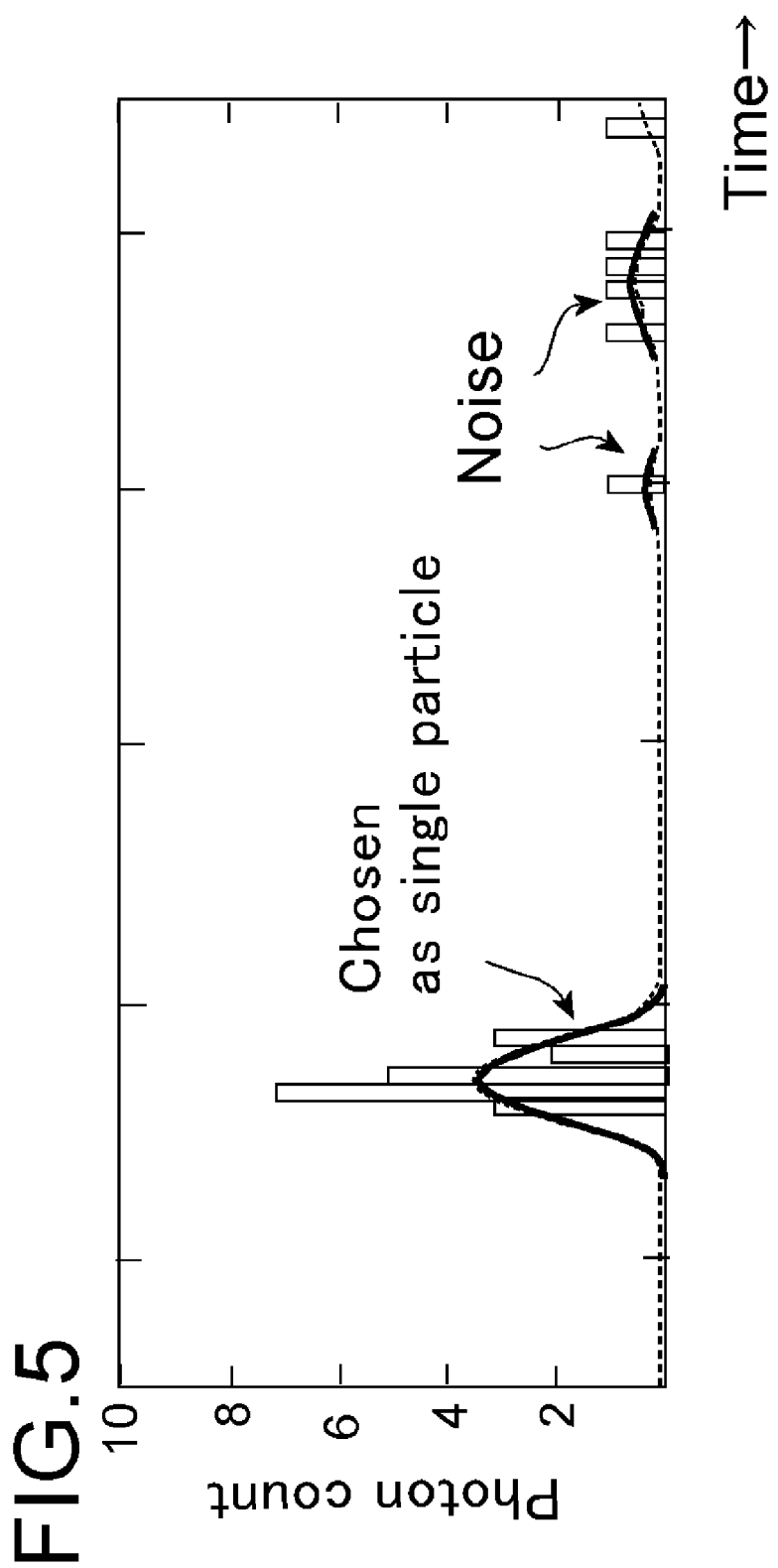

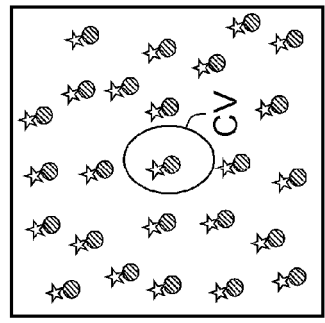
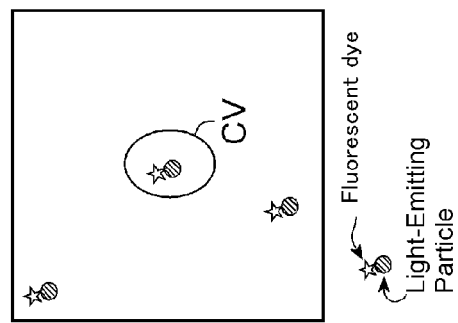
FIG.7A High Concentration (e. g. ~ 1nM)
FIG.7B Low Concentration (e. g. ~ 1pM)

OPTICAL ANALYSIS DEVICE AND OPTICAL ANALYSIS METHOD USING A WAVELENGTH CHARACTERISTIC OF LIGHT OF A SINGLE LIGHT-EMITTING PARTICLE

TECHNICAL FIELD

This invention relates to optical analysis device and method capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a device and a method of detecting the light from a single particle which emits light individually, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label has been attached, and the light emitted from a light-emitting particle may be fluorescence, phosphorescence, chemiluminescence, bioluminescence, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of µL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

By the way, generally, each light-emitting particle or light emitting label attached with a particle to be an observation object has a specific emission wavelength characteristic (emission spectrum), and thus, when the detection of light from a light-emitting particle or a light emitting label is performed so as to catch a feature of the emission wavelength characteristic of each light-emitting particle or light emitting label, the indentifying of the kind of light-emitting particle or light emitting label becomes possible. Therefore, in the above-mentioned scanning molecule counting method, by performing the detection of light from a light-emitting particle so that a feature of the emission wavelength characteristic of the light-emitting particle can be detected, it becomes advantageously possible to identify the kind of each single light-emitting particle detected individually.

In order to further develop the new optical analysis technique proposed in the above-mentioned patent applications 2010-044714 and PCT/JP2011/53481, the main object of the present invention is especially to propose novel optical analysis device and method enabling the identification of the kind of a detected single light-emitting particle by detecting a feature of the emission wavelength characteristic of the single light-emitting particle.

Solution to Problem

According to the present invention, the above-mentioned object is achieved by an optical analysis device which detects and analyzes light from a light-emitting particle dispersed and moving at random in a sample solution using an optical system of a confocal microscope or a multiphoton microscope, characterized by comprising a light detection region moving portion which moves a position of a light detection region of the optical system of the microscope in the sample solution by changing an optical path of the optical system; a light detecting portion which detects intensities of components of two or more wavelength bands of light from the light detection region; and a signal processing portion which detects individually signals from each light-emitting particle in the intensities of the components of two or more wavelength bands of the light detected with the light detection portion with moving the position of the light detection region in the sample solution, and identify a kind of the light-emitting particle based on the intensities of the components of two or more wavelength bands of light of the detected signals from the light-emitting particle. In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particles which emits light by phosphorescence, chemiluminescence, bioluminescence, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. When a light-emitting particle emits light without illumination light, for example, when a particle emits light by chemiluminescence or bioluminescence, no illumination light is not required in a microscope.) Further, in the followings in this specification, "a signal" means "a signal expressing light from a light-emitting particle" unless noted otherwise.

In the above-mentioned inventive device, similarly to the scanning molecule counting method, in the basic structure, the detection of the light from the light detection region is sequentially performed while the position of the light detection region is moved in the sample solution, namely, while the inside of the sample solution is scanned with the light detection region. Then, when the moving light detection region encompasses a randomly moving light-emitting particle, the light from the light-emitting particle is detected by the light detecting portion, and thereby, the existence of one particle will be detected. In this structure, in the case of the present invention, especially, the intensities of components of two or more wavelength bands of the light from the light detection region are measured. As already noted, light-emitting particles or light emitting labels attached with particles to be observation objects each have a specific emission wavelength characteristic and the feature in the emission wavelength characteristic can be grasped with reference to the intensities of components of two or more wavelength bands of the emitted light, and thus, it becomes possible to identify and specify the kind of each light-emitting particle based on the intensities of the components of two or more wavelength bands, measured as noted above. Thus, according to the above-mentioned structure, when a light-emitting particle enters into the moving route of the light detection region, the kind of the light-emitting particle or light emitting label can be individually identified from a feature of the emission wavelength characteristic, and also, it is advantageous that the detection of a light-emitting particle and identification of its kind are possible even when the light-emitting particle concentration in a sample solution is lower than the level required for obtaining a good measurement result in optical analysis techniques, such as FCS and FIDA.

In the above-mentioned structure, more concretely, a kind of light-emitting particle can be identified by referring to a ratio of the intensity distribution or an intensity ratio of components of two or more wavelength bands. Then, in one embodiment, the signal processing portion may be designed so that a kind of light-emitting particle may be identified based on a ratio of intensities of components of two or more wavelength bands of signals of light of a light-emitting particle. In this regard, it is advantageous that the number of the wavelength bands to be detected is small in respect of the ease of the wavelength selection in the light detection and signal processing, and therefore, typically, the above-mentioned inventive device may be so designed that the light detecting portion detects the intensities of components of two wavelength bands of light from the light detection region and the signal processing portion identifies a kind of light-emitting particle based on the ratio of the intensities of the component of the two wavelength bands. Taking into account an emission wavelength characteristic of a light-emitting particle or a light emitting label and detection sensitivity, etc., the wavelength band to be detected may be appropriately chosen so that a feature of the emission wavelength characteristic can be grasped as notably as possible.

Furthermore, especially in a case that a light-emitting particle is a particle which emits light with radiation of excitation light, the device is provided with a light irradiating portion for irradiating the light detection region with excitation light, and in that case, the light irradiating portion may radiate excitation light of one wavelength band, and the light detecting portion may detect the intensities of components of two or more wavelength bands of the light from the light detection region emitted with the radiation of the excitation light of one wavelength band. Usually, in measuring light in the optical system of a confocal microscope or a multiphoton microscope, a device is set so as to detect light of one wavelength band with radiation of excitation light of one wavelength band, and in measuring the light of light-emitting particles of two or more kinds together with identifying the kinds, the excitation lights of two or more wavelength bands are radiated. In that case, it is relatively difficult to make the condensing regions of the excitation lights of mutually different wavelength bands coincide with each other and to adjust the balance of the intensities of the excitation lights of two or more wavelength bands, and thus, the process of determining a value showing a feature of the emission wavelength characteristic of a light-emitting particle from the intensities of components of two or more wavelength bands will become cumbersome (The process for correcting the difference of the positions of the condensing regions of the excitation lights and the process for correcting the balance of the intensities of excitation lights will be needed.). However, when the excitation light is the light of one wavelength band, the process of determining a value showing a feature of the emission wavelength characteristic of a light-emitting particle can be simplified advantageously. Moreover, in a case of the irradiation of excitation light of one wavelength band, emitted light intensity may become comparatively low, depending on the excitation wave length characteristic of a light-emitting particle; however, in the case of the present invention, a kind of light-emitting particle is identified with reference to a feature of the emission wavelength characteristic of a light-emitting particle (more concretely, the ratio of the intensity distribution of components of two or more wavelength bands of light of a light-emitting particle), and thus, it should be understood that, when the accuracy of the ratio of the intensity distribution of components is ensured, the reduction of the absolute value of the intensity does not become a problem.

With respect to the moving of the position of the light detection region in the above-mentioned inventive structure, the moving speed of the position of the light detection region in the sample solution is appropriately changed based on the characteristic or the number density or concentration of the light-emitting particle in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the moving the position of the light detection region as described above, the moving speed of the position of the light detection region in the sample solution is preferably set to be higher than the diffusional moving velocity of a light-emitting particle (the average moving speed of a particle owing to the Brownian motion). As explained above, in the inventive device, the light detection region detects the light emitted from an encompassed light-emitting particle, so that the light-emitting particle will be detected individually. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal. In this regard, since the diffusional moving velocity differs depending upon light-emitting particles, it is preferable that the moving speed of the light detection region can be changed appropriately according to the characteristics of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement route of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow.). Further, since no structure for flowing a sample solution is required, the measurement and analysis can be conducted with a small amount of the sample solution (at the level of one to several tens of µL) similarly to FCS, etc.

Moreover, in an embodiment of the inventive optical analysis device, the signal processing portion may be designed to count the number of the signals of the light-emitting particle detected individually, thereby counting the number of the light-emitting particles detected during the moving of the light detection region. Then, it becomes possible to acquire the information on the number density or concentration of the light-emitting particle individually by the kind of light-emitting particle.

According to the above-mentioned inventive device, there is realized a new optical analysis method of detecting, with moving the position of a light detection region in a sample solution, the light of each light-emitting particle in a manner that the kind of light-emitting particle can be identified. Therefore, according to the present invention, there is provided an optical analysis method of detecting and analyzing light from a light-emitting particle dispersed and moving at random in a sample solution using an optical system of a confocal microscope or a multiphoton microscope, characterized by comprising steps of: moving a position of a light detection region of the optical system of the microscope in the sample solution by changing an optical path of the optical system; detecting intensities of components of two or more wavelength bands of light from the light detection region with moving the position of the light detection region in the sample solution; and detecting signals of light from each light-emitting particle individually in the intensities of the components of the two or more wavelength bands of the detected light and identifying a kind of the detected light-emitting particle based on the intensities of the component of the two or more wavelength bands of the signals of the light of the light-emitting particle.

Also in the above-mentioned method, the identification of a kind of light-emitting particle may be performed based on a ratio of the intensities of the components of the two or more wavelength bands of the signals of the light of the light-emitting particle, and especially, the intensities of the components of the two wavelength bands of the light from the light detection region may be detected, and the kind of light-emitting particle may be identified based on the ratio of the intensities of the components of the two wavelength bands. Further, in a case that a light-emitting particle is a particle which emits light with radiation of excitation light of one wavelength band, there may be performed a step of irradiating the light detection region with the excitation light of one wavelength band, and in the light detection process, the intensities of the components of two or more wavelength bands of the light from the light detection region emitted with the radiation of excitation light may be detected. Furthermore, also in the above-mentioned method, there may be comprised a step of counting the number of the individually detected light signals from the light-emitting particles to count the number of the light-emitting particles detected during the moving of the position of the light detection region and/or the step of determining the number density or concentration of the light-emitting particle in the sample solution based on the number of the detected light-emitting particles. Moreover, in the step of changing the optical path of the optical system in order to move the position of the light detection region, the position of the light detection region may be moved at a predetermined velocity or at a velocity quicker than the diffusion moving velocity of the light-emitting particle, and the moving speed of the position of the light detection region may be set based on a characteristic or the number density or concentration of the light-emitting particle in the sample solution.

The optical analysis technique in accordance with the present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, according to the present invention, in the scanning molecule counting method of detecting an existence of a light-emitting particle individually by scanning the inside of a sample solution with a light detection region in a confocal microscope or a multiphoton microscope, it becomes possible to identify the kind of each light-emitting particle by detecting the light of the light-emitting particle in a manner that a feature of the emission wavelength characteristic of the light-emitting particle can be grasped. According to this structure of the present invention, even in a case that two or more kinds of light-emitting particle are included in a sample solution, the kind of each light-emitting particle can be specified, and therefore, information about a condition, a number density or concentration of each particle in a system containing particles of two or more kinds, etc. is acquired, and also, from their change, detection and analysis of various phenomena, such as a binding and/or dissociative reaction or dispersion and aggregation of particles can be achieved. Further, in the present invention, since a light-emitting particle is individually detected and its kind is identified, even a light-emitting particle, whose concentration is relatively low in a sample solution so that the light of the light-emitting particle would be buried in the light from other light-emitting particles in the conventional methods, is detectable and its existence is observable. This feature is expected to be used for an application to detection of a product of a reaction having a comparatively low reaction rate or relatively low number of intermediate products.

Other purposes and advantages of the present inventions will become clear by explanations of the following preferable embodiments of the present invention.

BRIEF DESCRIPTIONS OF DRAWINGS

FIG. 1A is a schematic diagram of the internal structure of an optical analysis device realizing an optical analysis technique according to the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 2 A and 2B are a schematic diagram explaining the principle of the light detection and a schematic diagram of the variation of the measured light intensity with time in the scanning molecule counting method which constitutes a part of the optical analysis technique according to the present invention, respectively. FIG. 2C is a drawing explaining about the principle of enabling the identification of kinds of light-emitting particles from the difference in the emission wavelength characteristics of the light-emitting particles by detecting the intensities of the light components of two or more wavelength bands according to the present invention. The upper drawing shows emission wavelength characteristics of the light-emitting particles α, β, γ and δ having various, mutually different emission wavelength characteristics (emission spectra) (solid line graphs) and the ranges of two or more wavelength bands detected independently (observation windows—square frames under the abscissa designated with ch1-ch5). The bar graphs of the lower drawing schematically show the light intensities of the signals of the light-emitting particles α, β, γ and δ detected in the respective observation windows. FIG. 2D is a drawing similar to FIG. 2C, explaining that a kind of light-emitting particle can be identified when the light components of two wavelength bands are detected.

FIG. 3 is a drawing showing in the form of a flow chart the processes of the measurement to be performed according to the present invention.

Figure 4A:
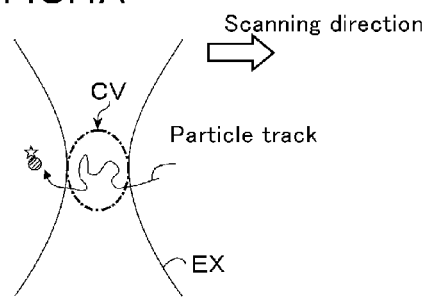
Figure 4B:
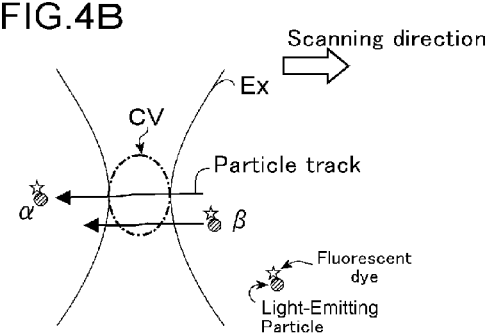
Figure 4C:
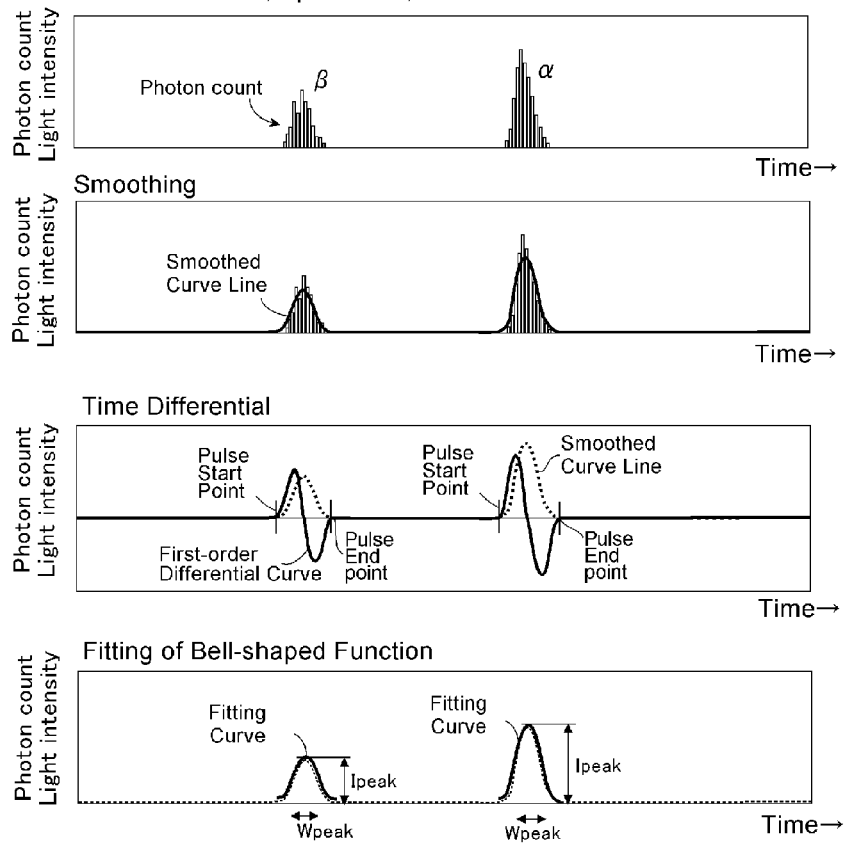

FIGS. 4A and 4B each are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining the example of the signal processing step of the detected signals in the procedure for detecting the existence of a light-emitting particle from the measured time series light intensity data (change in time of photon count) in accordance with the scanning molecule counting method.

FIG. 5 shows examples of measured photon count data (bar graph); curves obtained by carrying out the smoothing of the data (dotted line); and Gauss functions fitted on the pulse existing regions (solid line). In the drawing, the signals attached with "noise" are disregarded as signals due to noises or contaminants.

Figure 6A:
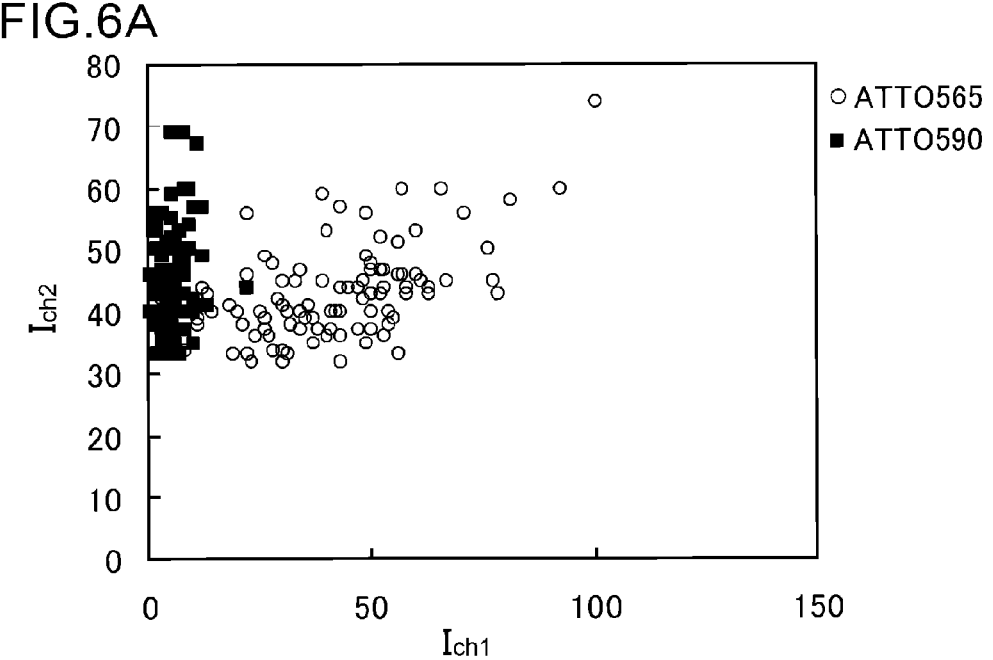
Figure 6B:
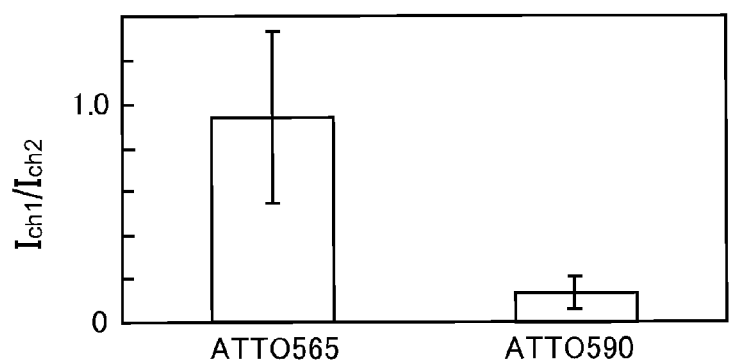

FIG. 6A is a drawing in which, with respect to a solution containing fluorescent dye ATTO565 and a solution containing fluorescent dye ATTO590, the light intensities (photon count) $I_{ch2}$ of the second wavelength band of each light-emitting particle detected according to this invention was plotted against the corresponding light intensities (photon counts) $I_{ch1}$ of the first wavelength band. In the drawing, each point corresponds to the intensities of one light-emitting particle. FIG. 6B shows the averages (bar graphs) and the standard deviations (error bars) of the ratios $I_{ch1}/I_{ch2}$ of the light intensities of two wavelength bands of the fluorescent dye ATTO565 and fluorescent dye ATTO590.

FIGS. 7A and 7B show examples of the time variation of the photon count (light intensity) obtained in a conventional optical analysis technique computing fluorescence intensity fluctuation, where FIG. 7A shows a case that the particle concentration is at a level providing a sufficient precision in the measurement, and FIG. 7B shows a case that the particle concentration in a sample is significantly lower than the case of FIG. 7A.

EXPLANATIONS OF REFERENCE NUMERALS

1—Optical analysis device (confocal microscope)
2—Light source
3—Single mode optical fiber
4—Collimating lens
5—Dichroic mirror
6, 7, 11—Reflective mirror
8—Objective
9—Micro plate
10—Well (sample solution container)
12—Condenser lens
13—Pinhole
14a b—Barrier filter
14x—Dichroic mirror for detected light
15—Multi-mode optical fiber
16a, b—Photodetector
17—Mirror deflector
17a—Stage position changing apparatus
18—Computer

DESCRIPTION OF EMBODIMENTS

In the followings, preferable embodiments of the present invention are described in detail.

Structure of Optical Analysis Device

In the basic structure, the present invention can be realized with an optical analysis device constructed by associating the optical system of a confocal microscope and photodetectors, enabling FCS, FIDA, etc., as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is then reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as a "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity reduced to $1/e^2$ of the peak intensity. Then, the light having passed through the pinhole 13 is divided into two or more wavelength bands with a dichroic mirror 14x (Although the light is divided into two wavelength bands in the drawing, it may be divided into two or more.), and the respective components of the divided light pass through the corresponding barrier filters 14a, b and a light component only in a specific wavelength band is selected; and then the light is introduced into a multimode fiber 15, reaching to the corresponding photodetector 16a, 16b (Although two photodetectors are equipped in the drawing, photodetectors of the number of detected wavelength bands may be equipped, and each of these may receive a component of one of the detected wavelength bands). With this structure, in the device of FIG. 1A, the components of two or more wavelength bands of the light from the light detection region are detected independently and simultaneously, and it becomes possible to capture a feature of the emission wavelength characteristic of a light-emitting particle. The photodetectors 16a, 16b convert the respective sequentially coming lights into time series electric signals and send them into the computer 18, and then, the processes for optical analysis are executed in a manner explained later. For the photodetectors 16a, 16b, preferably, super high sensitive photodetectors, usable for the photon counting, are used, so that the light from one light-emitting particle, for example, the faint light from one or several fluorescent dye molecule(s), can be detected.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetectors 16a, b under the control of the computer 18. The movement route of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence, the above-mentioned optical system of the confocal microscope is used as it is. Also, when a light-emitting particle emits light without excitation light with a chemiluminescence or bioluminescence phenomenon, the optical systems 2-5 for generating excitation light may be omitted. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Preferably, the excitation light radiated at a time is the light of one wavelength band, but the light of two or more wavelength bands may be used as the excitation light at a time depending upon an experimental condition.

Principle of the Present Invention

As described in the column of "Summary of Invention", according to the inventive optical analysis technique, briefly, in the "scanning molecule counting method" which detects an existence of a light-emitting particle dispersed in a sample solution individually by detecting the light emitted when the light-emitting particle is encompassed in a light detection region of a confocal microscope or a multiphoton microscope within the sample solution with moving the position of the light detection region, it is tried to measure components of two or more wavelength bands of the light of a light-emitting particle separately, and detect a feature of the emission wavelength characteristic of the light-emitting particle. According to this structure, it becomes possible to identify a kind of light-emitting particle from a feature of the emission wavelength characteristic of an individually detected light-emitting particle, and thus, in a system including light-emitting particles of two or more kinds, the detection of the existence of a light-emitting particle of each kind, the detection of the existence ratio (concentration ratio) of each kind of light-emitting particle and the acquisition of information, including the number densities or concentrations of each kind of light-emitting particle become possible. In the followings, the principles of the scanning molecule counting method and the detection of a feature of an emission wavelength characteristic in accordance with the present invention will be explained.

1. Principle of Scanning Molecule Counting Method

Spectral analysis techniques, such as FCS, etc., are advantageous in that the required sample amount is extremely small and a test can be performed promptly as compared with the conventional biochemical analytical techniques. However, in these spectral analysis techniques such as FCS, etc., the concentration and characteristics of a light-emitting particle are principally computed based on the fluorescence intensity fluctuation, and therefore, in order to obtain accurate measurement results, the concentration or number density of the light-emitting particle in a sample solution should be at the level where about one light-emitting particle always exists in a light detection region CV during the fluorescence intensity measurement as schematically drawn in FIG. 7A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn in FIG. 7B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring term should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, even when the concentration of the light-emitting particle is lower than the level requested in the above-mentioned spectral analysis techniques, such as FCS and FIDA.

Figure 2A:
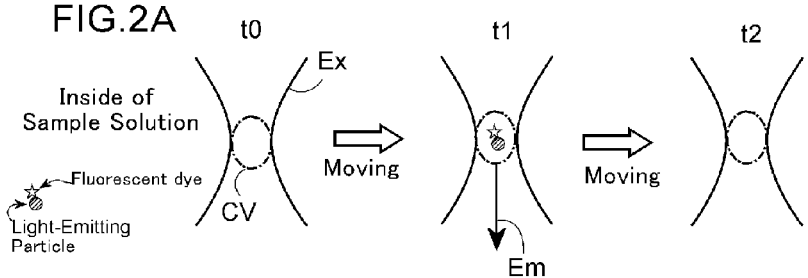
Figure 2B:
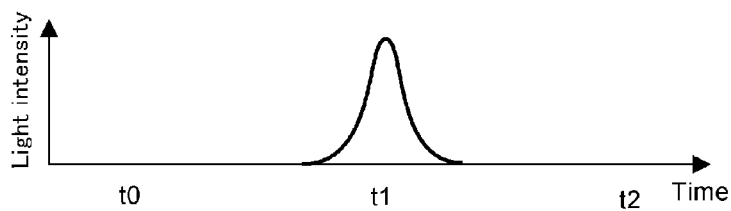

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2A. Then, for example, as in FIG. 2A, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and the characteristic of the light-emitting particle existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the characteristic of the particle is acquirable even in a sample solution with a low particle concentration at the level where no sufficiently accurate analysis is available in FCS, FIDA, etc.

Figure 2C:
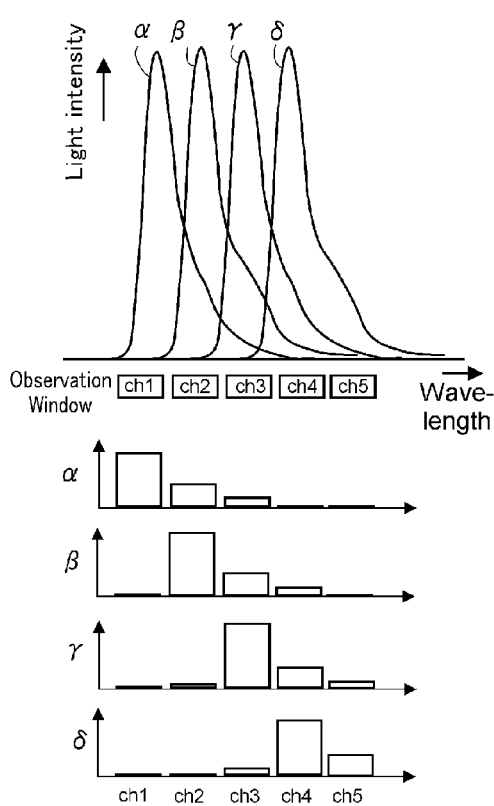
Figure 2D:
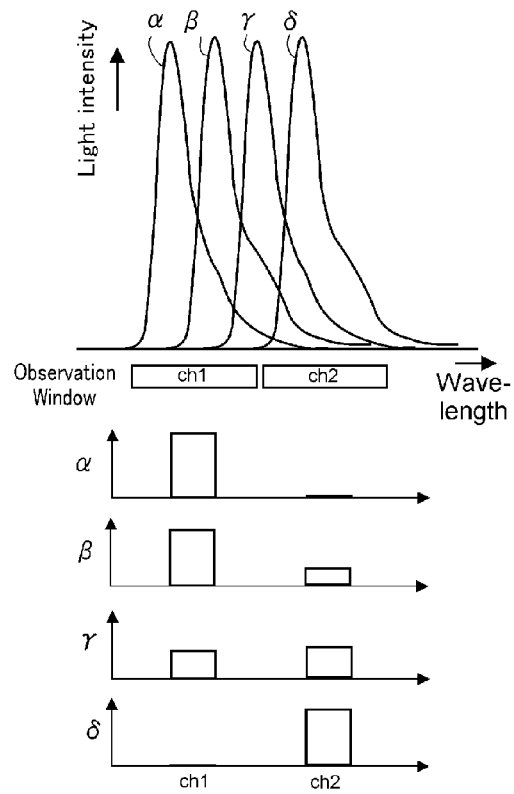

2. Principle of an Emission Wavelength Characteristic of a Light-Emitting Particle According to the Present Invention In order to detect a feature of the emission wavelength characteristic of a light-emitting particle or a light emitting label in the above-mentioned scanning molecule counting method, in the present invention, especially, the light from a light detection region is detected with being divided into two or more wavelength bands. For example, in a case that light-emitting particles α, β, γ and δ each having an emission wavelength characteristic (emission spectrum) as illustrated in FIG. 2C exist in a sample solution, when the light from the light detection region is divided into an adequate number of wavelength bands, e.g. into five observation windows ch1-ch5, and each of the components is measured with the corresponding separate photodetector, the distributions of the intensities of the ch1-ch5 of the light-emitting particle α, β, γ and δ having the respective emission wavelength characteristic become mutually different distributions reflecting features of the profiles of the emission wavelength characteristics as schematically drawn in FIG. 2C. Accordingly, with reference to the distribution of the intensities of ch1-ch5, e.g. the ratio of the intensities in the respective observation windows, $I_{ch1}:I_{ch2}:I_{ch3}:I_{ch4}:I_{ch5}$, which emission wavelength characteristic each light-emitting particle has will be found, and thereby the identification of the kind of the light-emitting particle becomes possible. For example, when the distribution of the intensities of ch1-ch5 of the signals of a certain light-emitting particle is the distribution of the graph indicated with "γ" of the lower part of FIG. 2C, the kinds of the light-emitting particle can be identified as a particle having the emission wavelength characteristic of γ.

In this connection, although it becomes possible to detect a feature of the emission wavelength characteristic of each light-emitting particle in detail as the number of observation windows i.e., the number of separately detected wavelength bands increases, the structure of the optical system (the dichroic mirror 14x, the barrier filter 14a, b, etc.) of the part for dividing the detected light of the device 1 becomes complicated and the cumbersomeness of the adjustment increases, and also, the intensity in each observation window will reduce and the accuracy of each measured intensity value may get worse. Thus, preferably, as in FIG. 2D, two observation windows may be employed and the detected wavelength band of each observation window may be adjusted so that a feature of the emission wavelength characteristic of each light-emitting particle may be appropriately reflected in the distribution of the intensities of the two observation windows, and then, based on the balance of the intensities in these two observation windows, the distinction of the kind of each light-emitting particle to be an observation object may be achieved. In that case, the identification of the kind of light-emitting particle may be done based on intensity ratio $I_{ch1}:I_{ch2}$ of two observation windows, $I_{ch1}/I_{ch2}$, etc.

Operation Processes

In the embodiment of the optical analysis in accordance with the present invention with the optical analysis device 1 as illustrated in FIG. 1A, concretely, there are conducted (1) a process of preparation of a sample solution containing light-emitting particles, (2) a process of measuring the light intensity of the sample solution and (3) a process of analyzing the measured light intensity. FIG. 3 shows the operation processes in this embodiment in the form of a flow chart.

(1) Preparation of a Sample Solution

The particle to be observed in the optical analysis technique of the present invention may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids.). Also, the particle to be observed may be a particle which emits light by itself, or may be a particle to which a light emitting label (a fluorescence molecule, a phosphorescence molecule, a chemi- and bioluminescent molecule) is attached in an arbitrary manner.

(2) Measurement of the Light Intensity of a Sample Solution

In the process of the measurement of the light intensity in accordance with the scanning molecule counting method of this embodiment, there is performed measuring the light intensity with driving the mirror deflector 17 to move the position of the light detection region within the sample solution (to scan in the sample solution) (FIG. 3-step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, the process of irradiating the light detection region with excitation light (only when it is necessary) and the process of detecting light from the light detection region during the moving of the position of the light detection region) memorized in a storage device (not shown), and then illuminating the light detection region in the sample solution with the excitation light (only when it is necessary) and measuring light intensity will be started. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetectors 16a, b each convert sequentially the receiving lights into electric signals and transmit them to the computer 18, which generates the time series light intensity data from the transmitted signals and store them in an arbitrary manner. The photodetectors 16a, b are typically super high sensitive photodetectors which can detect an arrival of a single photon, and thus the detection of light may be the photon counting performed in the manner of measuring sequentially the number of photons which arrive at the photodetector for every predetermined unit time (BIN TIME), for example, every 10 μs, during a predetermined time, and accordingly the time series light intensity data will be a time series photon count data.

Regarding the moving speed of the position of the light detection region, in order to perform quantitatively precisely individual detection of a light-emitting particle to be observed from the measured time series light intensity data in the scanning molecule counting method, preferably, the moving speed of the position of the light detection region during measurement of light intensity is set to a value quicker than the moving speed in the random motion, i.e., the Brownian motion of a light-emitting particle. When the moving speed of the position of the light detection region is slower than the movement of a particle owing to the Brownian motion, the particle moves at random in the region as schematically drawn in FIG. 4A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 4B, the moving speed of the position of the light detection region is set to be quicker than the average moving speed of a particle by the Brownian motion (diffusional moving velocity) so that the particle will cross the light detection region CV in an approximately straight line and thereby the profile of the change of the light intensity corresponding to each particle in the time series light intensity data becomes almost bell-shaped similarly to the excitation light intensity distribution as illustrated in the upper row of FIG. 4C and the correspondence between each light-emitting particle and light intensity can be easily determined.

Concretely, the time $\Delta\tau$ required for a light-emitting particle having a diffusion coefficient D to pass through the light detection region of radius r (confocal volume) by the Brownian motion is given from the expression of the relation of mean-square displacement:

$$(2\ r)^2 = 6\ D \cdot \Delta\tau \qquad (1)$$

as:

$$\Delta\tau = (2\ r)^2 / 6\ D \qquad (2)$$

and thus, the velocity of the light-emitting particle moving by the Brownian motion (diffusional moving velocity) Vdif, becomes approximately $$V\text{dif} = 2\ r/\Delta\tau = 3\ D/r \qquad (3)$$

Then, with reference to this, the moving speed of the position of the light detection region may be set to a value sufficiently quicker than Vdif. For example, when the diffusion coefficient of a light-emitting particle is expected to be about $D=2.0\times10^{-10}\ m^2/s$, Vdif will be $1.0\times10^{-3}\ m/s$, supposing r is about 0.62 μm, and therefore, the moving speed of the position of the light detection region may be set to its 10 times or more, 15 mm/s. In this regard, when the diffusion coefficient of a light-emitting particle is unknown, an appropriate moving speed of the position of the light detection region may be determined by repeating the execution of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of a light-emitting particle in a sample solution are obtained by the above-mentioned processes, detection of a signal corresponding to light from a light-emitting particle on the light intensity data and identification of the kind of each light-emitting particle may be performed in the computer 18 through processes in accordance with programs memorized in a storage device.

(i) Detection of a Signal Corresponding to a Light-Emitting Particle

When the track of one light-emitting particle in its passing through the light detection region is approximately straight as shown in FIG. 4B, the light intensity variation in the signal corresponding to the particle to be observed in the time series light intensity data has a bell shaped profile reflecting the light intensity distribution in the light detection region (determined by the optical system) (see the upper row of FIG. 4C). Thus, basically in the scanning molecule counting method, when the time width for which the light intensity exceeding an appropriately set threshold value continues is in a predetermined range, the signal having the profile of the light intensity may be judged to correspond to one particle having passed through the light detection region, and thereby one light-emitting particle is detected. And a signal whose time width for which the light intensity exceeding the threshold value continues is not in the predetermined range is judged as noise or a signal of a contaminant. Further, when the light intensity distribution in the light detection region can be assumed as Gaussian distribution:

$$I = A \cdot \exp(-2\, t^2/a^2) \quad (4)$$

and when the intensity A and the width a, computed by fitting Expression (4) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of operational methods of conducting collective detection of light-emitting particles from time series light intensity, a smoothing treatment is performed to the time series light signal data (FIG. 4C), the upper row "detected result (unsettled)") (FIG. 3-step 110, FIG. 4C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method, etc. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 4C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 4C), the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically a Gauss function, it may be a Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 5 left, is judged as a signal corresponding to one light-emitting particle, and thereby, one light-emitting particle will be detected. On the other hand, a pulse signal, whose computed parameters of the bell-shaped function are not within the assumed ranges, as shown in FIG. 5 right, is disregarded as noise.

The search and judgment of a pulse signal in the processes of the above-mentioned steps 130-150 may be repetitively carried out in the whole region of the time series light signal data of each of the components of two or more detected wavelength bands (Step 160). Further, in the case of this embodiment, the light of one light-emitting particle appears in the time series light intensity data of two or more detected wavelength bands, and thus, the signal of each light-emitting particle will be constituted by a group of signals in the time series light intensity data of two or more detected wavelength bands. In this regard, as understood from the lower drawings of FIG. 2C or 2D, the light of one light-emitting particle can appear in all of the time series light intensity data of two or more detected wavelength bands or only any of them. Thus, when a signal of a light-emitting particle appears in at least one of the time series light intensity data of two or more detected wavelength bands, the process may be done, considering that a signal of a light-emitting particle exists in the time series light intensity data of other detected wavelength bands at the time of the signal appearance. The associating of the signals on the time series light intensity data of the components of two or more detected wavelength bands may be done with reference to the time value of a pulse existing region. Furthermore, in an alternative manner, after signals of light-emitting particles are detected in one of the components of two or more detected wavelength bands, the process may be done, considering that, in the generation times of the detected signals on the time series light intensity data, signals of the light-emitting particles exist on the time series light intensity data of the other component(s) of the detected wavelength bands. Also, the process of detecting individually signals of light-emitting particles from time series light intensity data may be conducted by an arbitrary way other than the above-mentioned way.

(ii) Calculation of Light Intensity Ratio and Identification of the Kind of Each Light-Emitting Particle, (FIG. 3-Steps 170 and 180)

Thus, when the signals of a light-emitting particle are detected in time series light intensity data of each of the two or more detected wavelength bands, with reference to the light intensities of two or more detected wavelength bands for each light-emitting particle, the kind of light-emitting particle is judged based on their distribution. For the light intensity of each component, the peak intensity, the integrated value of photon counts of the signal of the light-emitting particle detected in steps 130-160 or the time integration value of the bell shaped function having been fit to the signal may be employed. For example, as shown in FIG. 2C, when the number of the detected wavelength bands is three or more, with reference to Those intensity ratios and: $(I_{ch1}/Io)$ $(I_{ch2}/Io):(I_{ch3}/Io):$—, based on the distribution of the ratios, the identification of the kind of light-emitting particle may be done (Io is the total of the intensities of the components of two or more detected wavelength bands.). Also, as in FIG. 2D, when the number of the detected wavelength bands is two, the value $I_{ch1}/I_{ch2}$ of those intensity ratio may be computed and the identification of the kind of light-emitting particle may be done with the computed value. And for a light-emitting particle whose ratio of the intensities of the components of two or more detected wavelength bands is previously known, the identification of its kind can be achieved from the intensity ratio computed above.

Furthermore, by counting the number of the signals of the detected light-emitting particles, the number of the light-emitting particles may be determined (counting of light-emitting particles). In that case, since kinds of light-emitting particles can be identified in the present invention, the number of light-emitting particles may be determined for each kind. Also, when the whole volume through which the light detection region passed is computed in an arbitrary way, the number density or concentration of light-emitting particles in a sample solution is determined from the volume value and the number of the light-emitting particles.

Although the whole volume through which the light detection region passed may be theoretically computed based on the wavelength of excitation light or a detected light, the numerical aperture of a lens and the adjustment condition of the optical system, the volume may be experimentally determined, for example, from the number of light-emitting particles detected by conducting the light intensity measurement, the detection of light-emitting particles and the counting thereof as explained above with a solution having a known light-emitting particle concentration (reference solution) under the same condition as that for the measurement of a sample solution to be tested, and the light-emitting particle concentration in the reference solution. Concretely, for example, supposing the detected number of the light-emitting particles is N in a reference solution of the light-emitting particle concentration C, the total volume Vt of the region which the light detection region has passed through is given by:

$$Vt = N/C \quad (5)$$

Alternatively, the plurality of solutions of different light-emitting particle concentrations are prepared as reference solutions and the measurement is performed for each of the solutions, and then, the average value of the computed Vt is determined as the total volume Vt of the region which the light detection region has passed through. Thus, when Vt is given, the concentration c of the light-emitting particle of the sample solution, whose counting result of the light-emitting particles is n, is given by:

$$c = n/Vt \quad (6)$$

In this regard, the volume of the light detection region and the total volume of the region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (5)) between concentrations C and light-emitting particle numbers N of various standard light-emitting particles for assumed moving patterns of the light detection region, so that a user of the device can appropriately use the memorized information on the relation in conducting an optical analysis. In this connection, since a kind of light-emitting particle can be identified in the present invention, the number density or concentration can be determined for each kind of light-emitting particle.

Thus, according to the above-mentioned present invention, in the scanning molecule counting method in which the inside of a sample solution is scanned with a light detection region and a light-emitting particle is individually detected, it becomes possible to identify the kind of each detected light-emitting particle by detecting the light of a light-emitting particle independently in two or more detected wavelength bands and referring to the intensity distribution or the intensity ratio in which a feature of the emission wavelength characteristic of the light-emitting particle is reflected.

In order to verify the validity of the present invention explained above, the experiments described below were conducted. In this regard, it should be understood that the following embodiments illustrate the validity of the present invention only, not intended to limit the scope of the present invention.

Embodiment 1

It was verified that the identification of a kind of light-emitting particle was possible in the scanning molecule counting method by the present invention.

For sample solutions, there were prepared solutions in which fluorescent dye ATTO565 (592 nm of fluorescence wavelength peaks) and ATTO590 (624 nm of fluorescence wavelength peaks) were dissolved to be at 100 pM of concentration in a phosphate buffer (including 0.05% Tween20), respectively (In the following, these are referred to as ATTO565 solution and ATTO590 solution.). In the light measurement, a single molecule fluorescence measuring apparatus MF-20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "(2) Measurement of the light intensity of a sample solution". In that time, a 500 µW laser light of 543-nm was used for excitation light, and the lights of the wavelength band of 565 to 595 nm (the first wavelength band—ch1); the wavelength band of 660 to 710 nm (the second wavelength band—ch2) were measured using band pass filters; and time series light intensity data were generated for the respective wavelength bands. The light detection region in the sample solution was moved at the moving speed of 15 mm/second. And, BIN TIME was set into 10 μsec. and measuring time was set to 2 seconds.

After the light intensity measurement, in accordance with the processes described in the above-mentioned "(3) (i) Detection of signals corresponding to a light-emitting particle", a smoothing treatment was applied to the time series light intensity data acquired in the ch2, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. Then, only the pulse signal satisfying the following conditions:

20 μsec.<pulse width<400 μsec.

Peak intensity>1.0 [pc/10 μsec.]

Correlation coefficient>0.95    (A)

was judged as a signal corresponding to a light-emitting particle, while a pulse signal which did not satisfy the above-mentioned conditions was disregarded as noise. Then, the integrated value of the photon counts on the time series light intensity data of ch1 and the integrated value of the photon counts on the time series light intensity data of ch2 in the generation period (pulse existing region) of the signal which was judged as a signal of a light-emitting particle on time series light intensity data of ch2 were computed as the intensity value Ich1 of ch1 and the intensity value Ich2 of ch2 of the signal of the light-emitting particle FIG. 6A is a drawing in which, for the signals of light-emitting particles detected in the above-mentioned light measurement and signal detection process of the ATTO565 solution and ATTO590 solution, the intensities Ich2 of ch2 are plotted against the intensity Ich1 of ch1. As understood from the drawing, the plots (white circle) of ATTO565 and the plots (black square) of ATTO590 were distributed approximately on the lines, respectively, and the two distributions were mutually separated. This indicates that an intensity ratio Ich1/Ich2 is a value reflecting a feature of the emission wavelength characteristic of each fluorescent dye and specific to a kind of light-emitting particle, and that a kind can be recognized with the intensity ratio. FIG. 6B shows the average (bar graph) and standard deviation (error bar) of each of the intensity ratio Ich1/Ich2 of ATTO565, and the intensity ratio Ich1/Ich2 of ATTO590, and as understood from the drawing, the average of the intensity ratio of ATTO565 and the average of the intensity ratio of ATTO590 significantly differ from one another, and the error bar of the intensity ratio of ATTO565 and the error bar of the intensity ratio of ATTO590 do not overlap with one another, and accordingly, it has been shown that a signal of ATTO565 and a signal of ATTO590 can be discriminated mutually.

Thus, as understood from the results of the above-mentioned embodiment, according to the above-mentioned present invention, in the scanning molecule counting method, by measuring components of two or more detected wavelength bands independently, and referring to the intensity ratio of the components of the two or more detected wavelength bands in which a feature of the emission wavelength characteristic of a light-emitting particle, it becomes possible to distinguish signals of light-emitting particles in accordance with the kind of detected light-emitting particle, and thereby, the identification of the kind of each light-emitting particle becomes possible. Especially, in the present invention, a signal of a light-emitting particle is detected individually and the identification of the kind of each light-emitting particle becomes possible, and therefore, even when the light-emitting particle concentration in a sample solution is lower than the concentration range requested in optical analysis techniques, such as FCS, the detection of a light-emitting particle is possible, and this feature is advantageous in conducting an analysis of a rare or expensive sample often used in the field of the research and development of Medicine and/or Biology. Moreover, since the identification of a kind of light-emitting particle becomes possible by the present invention, it is expected that the application area of the scanning molecule counting method will be expanded.

The invention claimed is:

1. An optical analysis device which detects and analyzes light from a light-emitting particle dispersed and moving at random in a sample solution using an optical system of a confocal microscope or a multiphoton microscope, the device comprising:
a light detection region moving portion which moves a position of a light detection region of the optical system in the sample solution by changing an optical path of the optical system;
a light detecting portion which detects intensities of components of two or more wavelength bands of light from the light detection region; and
a signal processing portion which detects individually signals from each light-emitting particle in the intensities of the components of the two or more wavelength bands of the light detected with the light detection portion with moving the position of the light detection region in the sample solution, and identifies a kind of the detected light-emitting particle based on the intensities of the components of the two or more wavelength bands of the signals of the light of the light-emitting particle.

2. The device of claim 1, wherein the signal processing portion identifies the kind of the light-emitting particle based on the ratio of the intensities of the components of the two or more wavelength bands of the signals of the light of the light-emitting particle.

3. The device of claim 1, wherein the light detecting portion detects intensities of components of two wavelength bands of light from the light detection region, and the signal processing portion identifies the kind of the light-emitting particle based on the ratio of the intensities of the components of the two wavelength bands.

4. The device of claim 1, further comprising a light irradiating portion which irradiates the light detection region with excitation light of one wavelength band, and wherein the light-emitting particle is a particle which emits light with radiation of the excitation light of the one wavelength band and the light detecting portion detects intensities of components of two or more wavelength bands of light from the light detection region emitted with the radiation of the excitation light of the one above-mentioned wavelength band.

5. The device of claim 1, wherein the signal processing portion counts a number of the signals of the lights of the light-emitting particles detected individually to count a number of the light-emitting particles detected during the moving of the position of the light detection region.

6. The device of claim 1, wherein the light detection region moving portion moves the position of the light detection region at a velocity quicker than a diffusional moving velocity of the light-emitting particle.

7. An optical analysis method of detecting and analyzing light from a light-emitting particle dispersed and moving at random in a sample solution using an optical system of a confocal microscope or a multiphoton microscope, the method comprising steps of:

moving a position of a light detection region of the optical system in the sample solution by changing an optical path of the optical system;

detecting intensities of components of two or more wavelength bands of light from the light detection region with moving the position of the light detection region in the sample solution; and detecting signals from each light-emitting particle individually in the intensities of the components of the two or more wavelength bands of the detected light and identifying a kind of the detected light-emitting particle based on the intensities of the components of the two or more wavelength bands of the signals of the light of the light-emitting particle.

8. The method of claim 7, wherein the kind of the light-emitting particle is identified based on the ratio of the intensities of the components of the two or more wavelength bands of the signals of the light of the light-emitting particle.

9. The method of claim 7, wherein intensities of components of two wavelength bands of light from the light detection region are detected, and the kind of the light-emitting particle is identified based on the ratio of the intensities of the components of the two wavelength bands.

10. The method of claim 7, further comprising a step of irradiating the light detection region with excitation light of one wavelength band, and wherein the light-emitting particle is a particle which emits light with radiation of the excitation light of the one wavelength band and intensities of components of two or more wavelength bands of light from the light detection region emitted with the radiation of the excitation light of the one above-mentioned wavelength band are detected.

11. The method of claim 7, further comprising a step of counting a number of the signals of the lights of the light-emitting particles detected individually to count a number of the light-emitting particles detected during the moving of the position of the light detection region.

12. The method of claim 7, wherein, in the step of moving the position of the light detection region, the position of the light detection region is moved at a velocity quicker than a diffusional moving velocity of the light-emitting particle.

* * * * *